United States Patent [19]
Reinhardt et al.

[11] Patent Number: 6,007,508
[45] Date of Patent: Dec. 28, 1999

[54] EPICONDYLITIS CLASP

[75] Inventors: Holger Reinhardt; Hans Bruno Bauerfeind, both of Kempen, Germany

[73] Assignee: Bauerfeind Orthopadie GmbH & Co. KG, Germany

[21] Appl. No.: 09/063,093

[22] Filed: Apr. 21, 1998

[30] Foreign Application Priority Data

Apr. 21, 1997 [DE] Germany .......................... 197 16 705

[51] Int. Cl.$^6$ .............................. A61F 13/00; A61F 5/00
[52] U.S. Cl. ................... 602/62; 602/5; 602/20
[58] Field of Search .................... 602/20, 21, 19, 602/5, 62; 128/878, 881, 892; 606/201, 203, 204

[56] References Cited

U.S. PATENT DOCUMENTS

| | | | |
|---|---|---|---|
| 4,182,318 | 1/1980 | Beige et al. | 602/20 |
| 4,188,944 | 2/1980 | Augustyniak | 602/20 |
| 5,069,457 | 12/1991 | Korzenowski | 128/881 |
| 5,295,951 | 3/1994 | Fareed | 602/62 |
| 5,385,537 | 1/1995 | Davini | 602/21 |
| 5,410,756 | 5/1995 | Hutson | 602/20 X |

FOREIGN PATENT DOCUMENTS

| | | |
|---|---|---|
| 26 35 426 | 10/1982 | Germany . |
| 91 15 993 | 4/1992 | Germany . |
| 93 16 368 | 4/1994 | Germany . |

*Primary Examiner*—Richard J. Apley
*Assistant Examiner*—Denise Pothier
*Attorney, Agent, or Firm*—Banner & Witcoff, Ltd.

[57] ABSTRACT

The invention relates to an epicondylitis clasp having a brace which contains a spring strip and can be contracted by an infinitely adjustable retaining strap. Arranged at one end of the brace on the inside of the clasp is a pad which serves to exert pressure on the epicondyle, is configured as an elongated, roughly rectangular cushion, having a longitudinal direction transverse to the clasping direction of the brace and a widened part at one end, and is fastened rotatively to the clasp via a central axis perpendicular to the longitudinal direction of the pad in such a way that the widened part points toward the upper arm, whether applied to the right or left arm.

8 Claims, 4 Drawing Sheets

EPICONDYLITIS CLASP

FIELD OF THE INVENTION

The invention relates to an epicondylitis clasp having a brace which contains a spring strip and can be contracted by an infinitely adjustable retaining strap.

BACKGROUND OF THE INVENTION

Such an epicondylitis clasp is disclosed in DE W 26 35 426 C2, which contains a brace having a roughly semicircular spring and has at its one end a pressure plate which presses against the forearm when the brace is tightened by means of a retaining strap provided with a touch-and-close fastener, but without exerting a special pressure in this region in the process, since the clasp has no cushion or pad.

Another epicondylitis clasp is disclosed in DE 9115993 U1. This clasp contains a bow-shaped brace whose ends can be drawn together by means of a retaining strap, the brace being contracted around the relevant region of the forearm. A pad provided on the inside of the brace presses in this case onto the part of the forearm to which it is applied and is intended to develop its therapeutic effect thereby.

Finally, reference may be made to DE 9316368 U1, in which an epicondylitis clasp is disclosed which essentially comprises a strip-shaped bandage on whose inside two displaceable pressure cushions are fitted. The bandage can be tightened by means of a retaining strap, the cushion pushed onto the desired point exerting a pressure on the epicondyle in order to influence it therapeutically.

BRIEF SUMMARY OF THE INVENTION

It is the object of the invention to create an epicondylitis clasp wherein it is possible to introduce pressure in an adjustable fashion onto the epicondyle in a way which is particularly favorable therapeutically independently of whether the clasp is applied to the right or left arm.

DETAILED DESCRIPTION OF THE INVENTION

Figure 1:
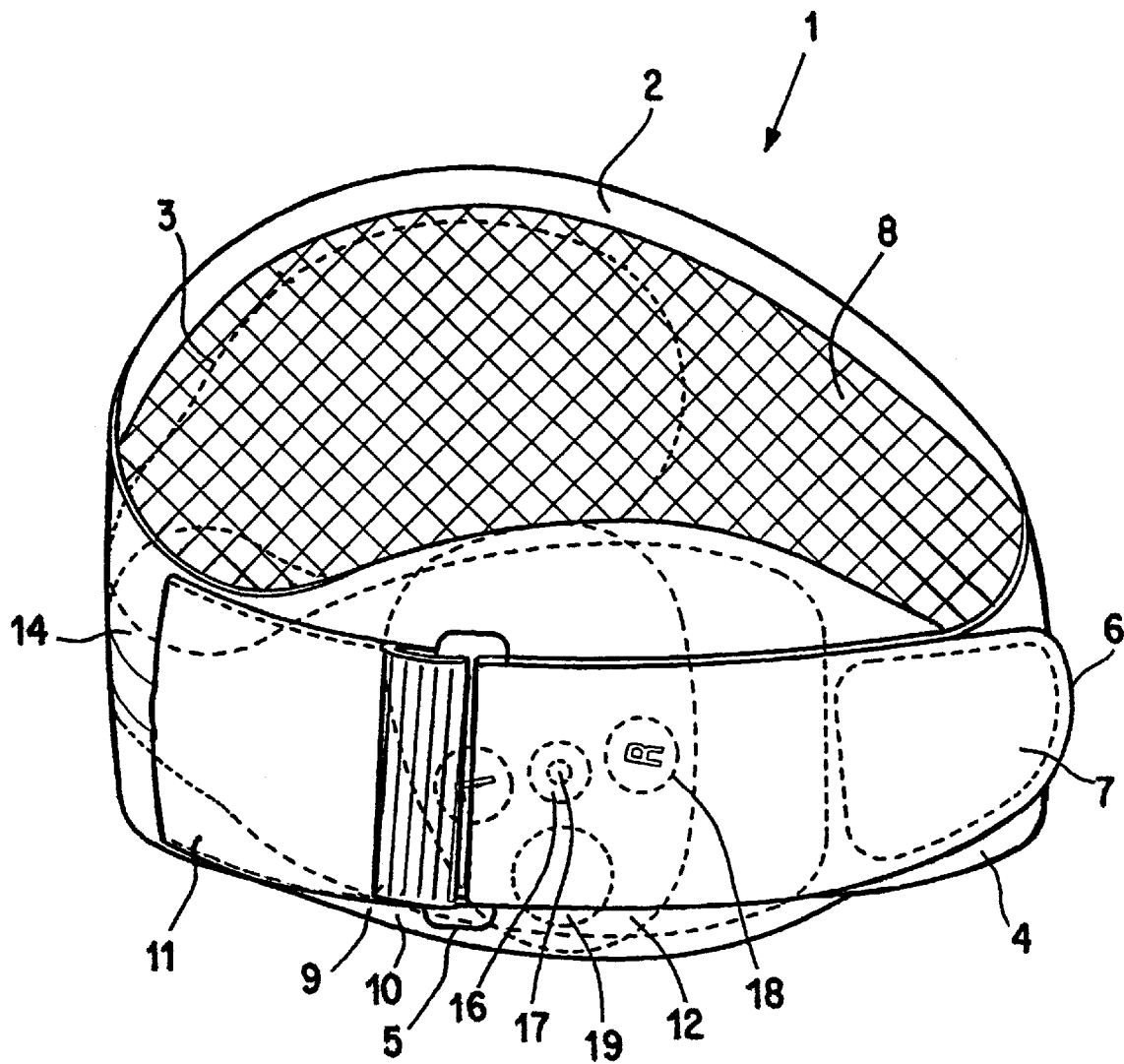

According to the invention, this is brought about by virtue of the fact that arranged at the one end of the brace on the inside of the clasp is a pad which serves to exert pressure on the epicondyle, is configured as an elongated, roughly rectangular cushion, having a longitudinal direction transverse to the clasping direction of the brace and a widened part at one end, and is fastened rotatively to the clasp via a central axis perpendicular to the longitudinal direction of the pad in such a way that the widened part points toward the upper arm, whether applied to the right or left arm.

The pad arranged on one end of the brace and having the form of the elongated, triangular cushion has proved to be a structure which has a particularly intensive action, takes account of the anatomical relationships on the forearm and creates on the outside of the forearm in the direction of the elbow a therapeutically desired wider pressure surface by comparison with a narrower pressure surface in the direction away from the elbow. The rotatability of the pad renders it possible here for it to be adjusted in each case transverse to the longitudinal direction of the brace in such a way that the widened side at one end of the pad is situated either on the left-hand or on the right-hand side of the brace, specifically when looking onto the inside of the brace. The epicondylitis clasp can thus be used universally on the right or left forearm and with a high therapeutic effect.

In order to concentrate the pressure effect originating in this epicondylitis clasp particularly onto the region of the pad, its brace is expediently configured in such a way that the end of the brace bearing the pad is joined to the further region of said brace via a weakened part of the spring strip which bends like a hinge when the clasp is applied and the retaining strap is tightened, and presses the pad against the arm. The weakened part of the spring strip lends the latter a certain hinging effect at the point of the weakening, with the result that although tightening the retaining strap does contract the brace as a whole, because of the hinging effect the end of the brace bearing the pad is drawn particularly toward the forearm and thereby increases the pressure effect in this region.

The retaining strap is expediently hinged in the region of the weakened part to the brace via a deflecting element which is fastened to the brace via an elastic band, it being the case that as it expands the elastic band introduces the tension thereby produced into the region of the pad via the deflecting element. As a result of this arrangement of the deflecting element and of the elastic band, there is a particularly favorable introduction of the pressure exerted by the epicondylitis clasp.

In order to render visible the tension produced by the epicondylitis clasp when it is applied, the elastic band is expediently guided in a pocket provided on the brace and is provided with markings which, by becoming visible, indicate the tension of the elastic band as it expands.

The abovementioned weakened part of the spring strip contained in the brace can, moreover, be utilized to permit the end of the brace bearing the pad the possibility of twisting with respect to the further region of the brace. Twisting of the region of the brace having the pad is particularly desirable because of the anatomy of the forearm.

In order to intensify the therapeutic effect of the cushion forming the pad, the latter is advantageously provided at each of its three corners with a raised portion, which then exerts a particularly concentrated pressure in its region. This exertion of pressure can be further intensified by providing the raised portions with a profiled surface.

It is advantageously possible to provide on the end of the brace bearing the pad a viewing window which indicates, as a function of the torsion of said pad whether the pad is set for applying to a right or left arm.

Figure 2:
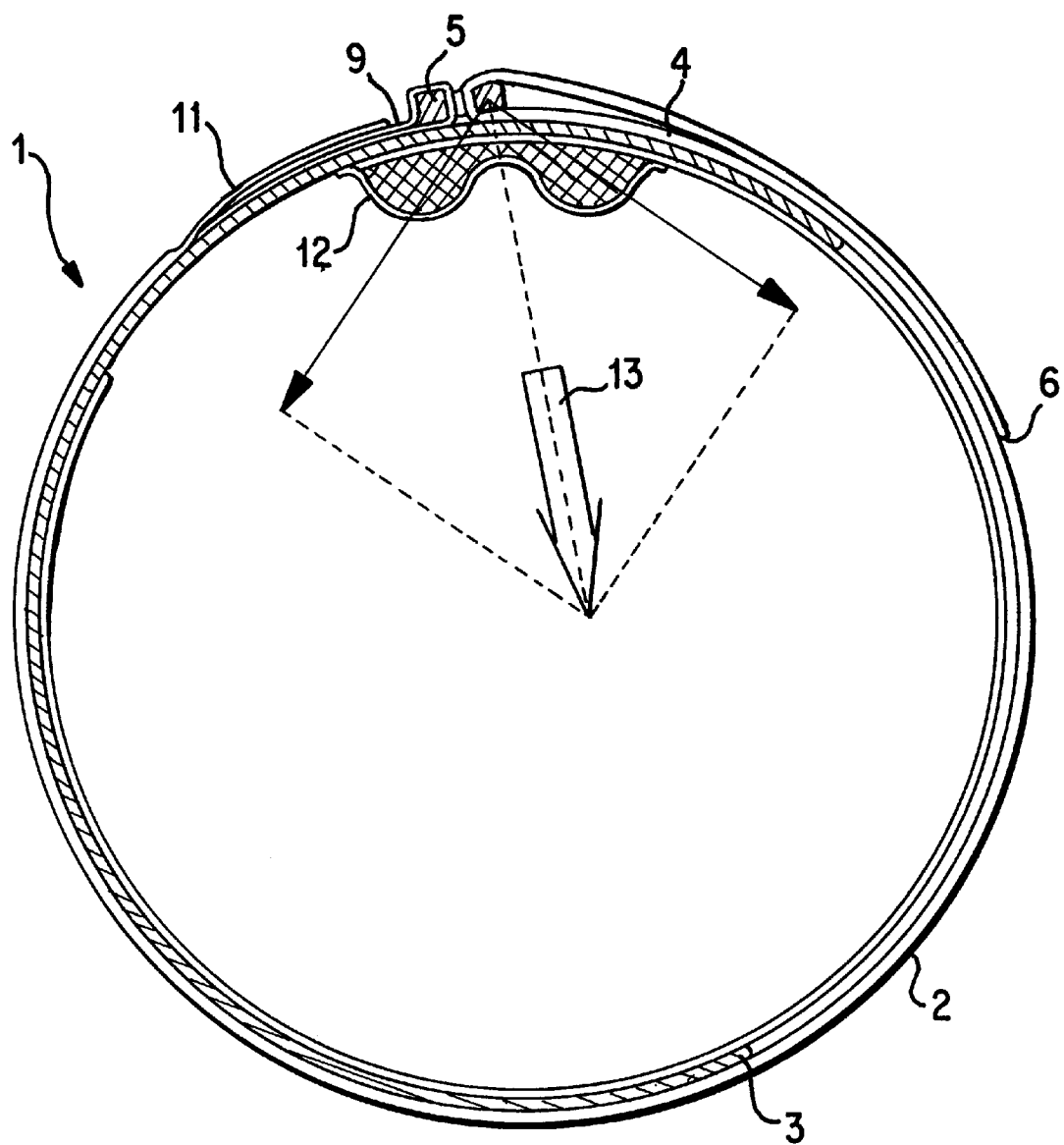
Figure 3:
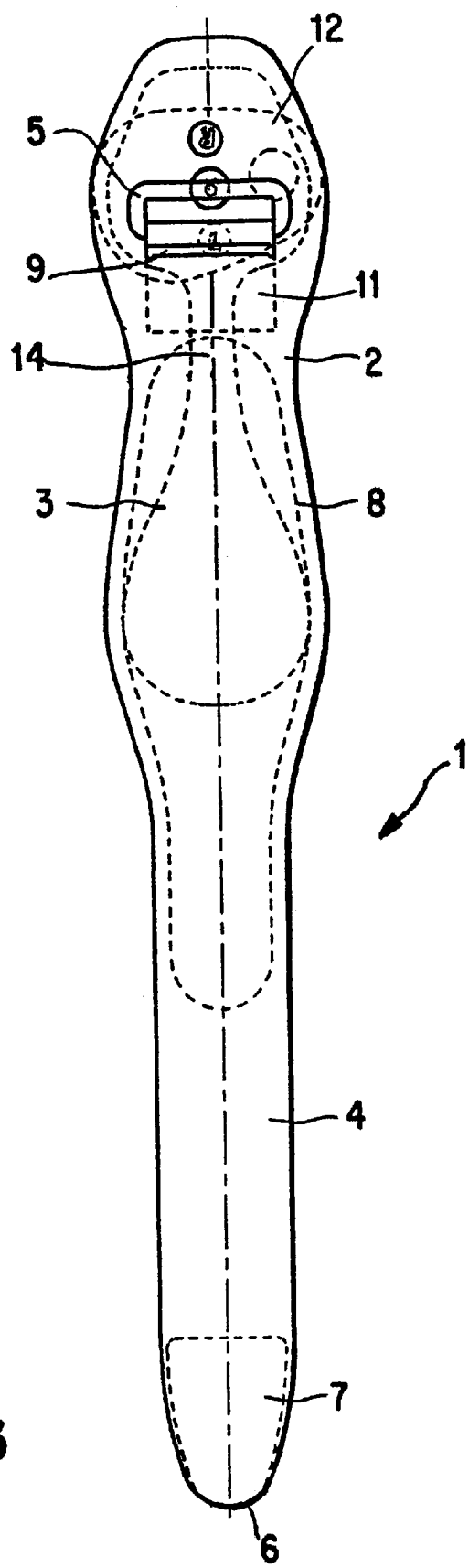
Figure 4:
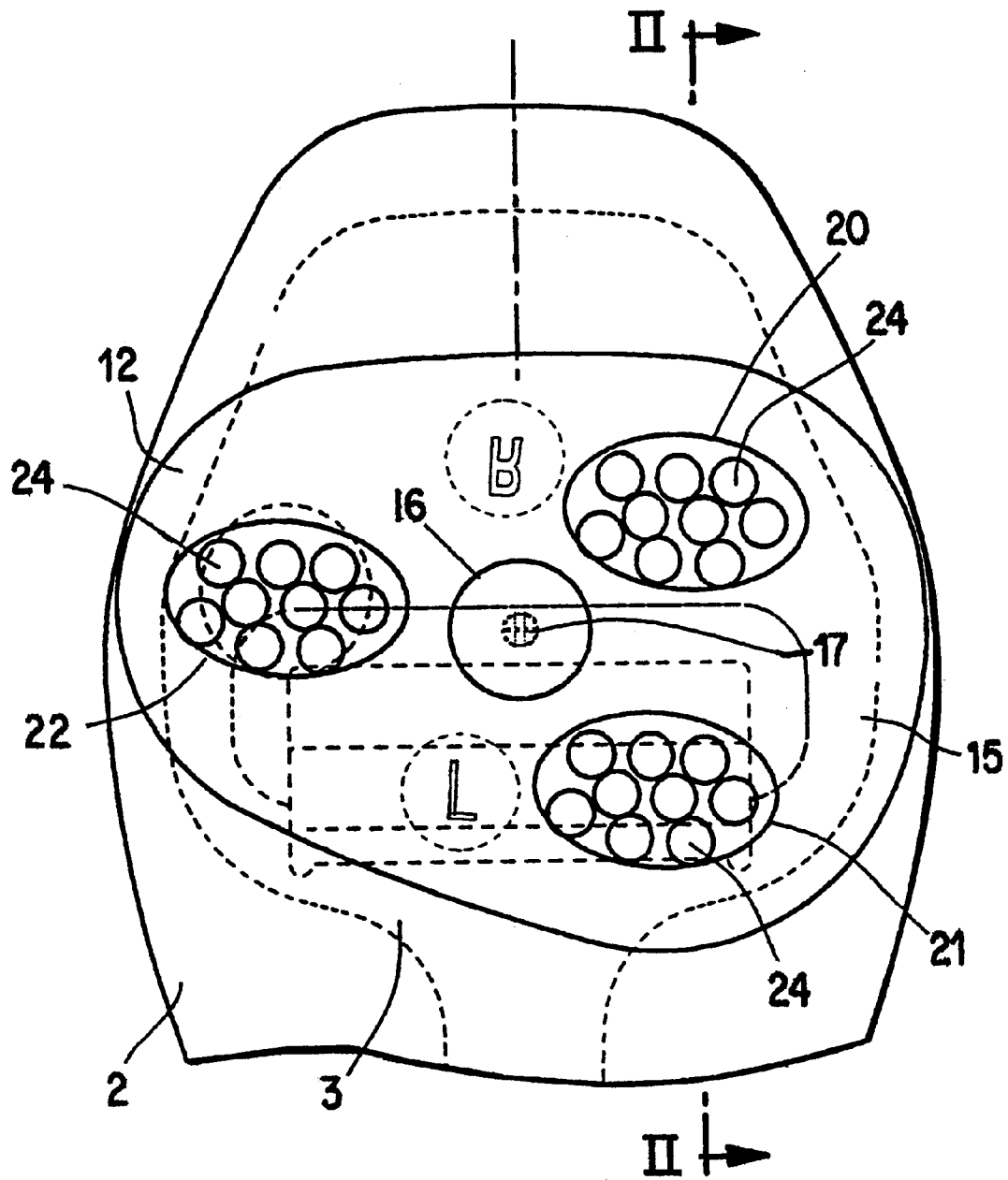

An exemplary embodiment of the invention is represented in the figures, in which:

FIG. 1 shows the epicondylitis clasp in a perspective view, with a retaining strap which tightens the brace, FIG. 2 shows the epicondylitis clasp in accordance with FIG. 1 in an axial view and in a section along the line A—A from FIG. 4, FIG. 3 shows the epicondylitis clasp in open position and in a stretched development, and FIG. 4 shows an internal view of the epicondylitis clasp in the region of the pad.

FIG. 1 shows the epicondylitis clasp 1, which comprises the brace 2 with the spring strip contained therein. The spring strip 3 is bonded into the brace 2 in the way described further below. The brace 2 merges into the retaining strap 4, which is narrower than the brace 2, and, in the representation shown closed in accordance with FIG. 1, is looped through the deflecting element 5 in the form of a stretched ring and is laid with its end 6 over the start of the retaining strap 4, where it is held in place by means of the touch-and-close fastener 7 on the retaining strap 4. The brace 2 is provided on its inside with a textile support 8 (crosshatched), which facilitates the wearing of the epicondylitis clasp.

The deflecting element 5 is fastened to the brace 2 via the elastic band 9, which is provided with a plurality of transverse seams 10 for the reasons represented further below. On its side averted from the deflecting element, the elastic band 9 extends in the pocket 11 provided on the brace 2, in which pocket it is fastened to the brace 2. The brace 2 envelopes the spring strip 3 contained in it with a covering of textile material which merges into the retaining strap 4 and forms the hairy part for the touch-and-close fastener 7 with its bur elements.

FIG. 1 also shows a pad, which is drawn with dashes, designed as a cushion 12, arranged on the inside of the brace 2 in the position of the epicondylitis clasp 1 drawn as closed, and is therefore represented as invisible in FIG. 1. More detail will be given further below on the cushion in connection with FIG. 4.

FIG. 2 shows the epicondylitis clasp 1, represented in FIG. 1, in an axial view, specifically in a section along the line A—A of FIG. 4. It is clear from FIG. 2 how the end 6 is held in place by the retaining strap 4, which is looped around the deflecting element 5 and bears with its end 6 against the relevant part of the retaining strap 4, where it is held in place by the action of the touch-and-close fastener 7 represented in FIG. 1. Worked into the brace 2 is the spring strip 3, which extends over the largest part of the brace 2 and lends the latter a desired flexible stiffness.

FIG. 2 also shows the fastening of the deflecting element 5 via the elastic band 9 in the pocket 11, from which the elastic band 9 projects over a short distance. In accordance with the parallelogram of forces illustrated in FIG. 2, the influence of the tension exerted on the deflecting element by the turned-back end 6 of the retaining strap 4 produces a force, represented by the arrow 13, which acts on the part of the forearm opposite the cushion 12. In order to achieve the desired therapeutic effect in this case, the epicondylitis clasp 1 represented is applied to the forearm in such a way that the cushion 12 is arranged in the position with respect to the epicondyle which is desired by the attending physician.

FIG. 3 shows the epicondylitis clasp 1 represented in FIGS. 1 and 2 in a position of stretched development, specifically in a plan view of the deflecting element 5 visible from the outside, with the spring strip 3, which is drawn in with dashes and here exhibits the weakened part 14, by means of which the spring strip 3 is substantially reduced by comparison with its end regions. Because of this weakened part 14 of the spring strip 3, the former lends the spring strip 3 a certain hinging effect in the region of the weakened part 14, with the result that when the retaining strap 4 is pulled on tight the part, bearing the pad 12, of the base 2 bends off inwards with respect to what is otherwise a round brace 2, and is thus capable of exerting a particular pressure on the part of the forearm situated at this point in the direction of the arrow 13 represented in FIG. 2. Furthermore, the weakened part 14 makes it possible for the brace 2 to twist with its part bearing the cushion 12 with respect to the further region of the brace 2, in order thus to be able to adapt comfortably to the shape of the forearm.

The effect of the tension on the deflecting element 5 produced by turning back the end 6 of the retaining strap 4 is that the elastic band 9, by which the retaining strap 4 is held, is drawn out, because of its elasticity, from the pocket 11 in accordance with the tension exerted by the retaining strap 4, it being the case that a greater or lesser number of transverse seams 10 (see FIG. 1) appear whose number can thus be used to read off the relevant tensile force and, via the latter, the pressure exerted on the forearm. Of course, it is also possible to use various colored strips instead of the transverse seams 10.

The end of the brace 2 bearing the cushion 12 is represented in FIG. 4, specifically in a view from inside, with the result that the cushion 12 is directly visible. The cushion 12 has a contour resembling a triangle with a widened part 15 on one side, the cushion 12 being arranged, transverse to the longitudinal direction of the brace 2, in its longitudinal extent specified by the triangular shape. The cushion 12 is held rotatably on the brace 2 via the axis 17 formed by the rivet 16, the rivet 16 ensuring that the cushion 12 bears tightly against the brace 2 while maintaining its ability to rotate. On its side facing the brace 2, the cushion 12 has the two markings "R" and "L", which indicate whether they belong to the right or left arm. These markings can be seen through a window 18 (see FIG. 1) in the brace 2, with the result that the user of the epicondylitis clasp recognizes at once, depending on the rotation of the cushion 12, whether the clasp is set for the right or left arm. Also indicated in FIG. 1, by the circle 19 drawn with dashes, is a bonding point via which the cushion 12 is held in the position respectively set.

It may be seen from the construction of the cushion 12 represented in FIG. 4 that said cushion is provided in each case at its corners formed by the approximate triangular shape with a raised portion 20, 21 and 22 which effects a particular therapeutic effect owing to the exertion of an increased pressure on the relevant points. Moreover, the three raised portions 20, 21 and 22 are provided with knobs 24 by means of which, as profiled surface, a particularly therapeutic effect is likewise achieved. However, it may be pointed out that the cushion can also be provided with a continuous simple camber formed around the rivet 16.

We claim:

1. An epicondylitis clasp (1) comprising a brace (2) having an inside and a clasping direction along a length of the brace, an a spring strip (3) and a retaining strap (4) providing infinite adjustment to the clasp, a pad (12) secured at an end of the brace (2) on the inside of the brace (2) to exert pressure on the epicondyle, the pad being an elongated, generally triangular cushion, having a longitudinal direction transverse to the clasping direction of the brace (2), said pad further having a widened part (15) at a first end, and a fastener rotatively fastening the pad to the brace (2), about a central axis (17) perpendicular to the longitudinal direction of the pad so that the widened part (15) points toward the upper arm, whether applied to the right or left arm.

2. The clasp as claimed in of claim 1, wherein the spring strip (3) includes a weakened part (14) at said end of the brace which bends like a hinge when the clasp (1) is applied and the retaining strap (4) is tightened to press the pad (12) against the arm.

3. The clasp as claimed in of claim 2, which further includes a deflecting element and an elastic band, wherein the retaining strap (4) is hinged to the brace (2) near the weakened part via the deflecting element (5), the deflecting element is fastened to the brace (2) via the elastic band (9), and the elastic band (9) expands and introduces tension (13) into the region of the pad (12) via the deflecting element (5).

4. The clasp as claimed in of claim 3, which the brace further includes a pocket to guide the elastic band (9) and the elastic band is provided with markings (10) which become visible to indicate the tension of the elastic band (9) as it expands.

5. The clasp as claimed in any one of claims 2 to 4, wherein the weakened part (14) permits the end bearing the pad (12) to twist with respect to the further region of the brace (2).

6. The clasp as claimed in any one of claims 1 to 4, wherein the pad (12) has a raised portion (20, 21, 22) at each of its three corners.

7. The clasp as claimed in claim 6, wherein the raised portions (20, 21, 22) each have a profiled surface (24).

8. The clasp as claimed in any one of claims 1 to 4, wherein a viewing window (18) is provided on the end of the brace (2) bearing the pad (12), and the pad includes markings visible through the window to indicate the orientation of pad on the brace.

* * * * *